(12) United States Patent
Patel

(10) Patent No.: US 8,609,684 B2
(45) Date of Patent: Dec. 17, 2013

(54) SOLUBILIZATION AND BIOAVAILABILITY OF ACETAMINOPHEN

(75) Inventor: Bhiku G. Patel, Chandler, AZ (US)

(73) Assignee: PruGen IP Holdings, Inc., Scottsdale, AZ (US)

( * ) Notice: Subject to any disclaimer, the term of this patent is extended or adjusted under 35 U.S.C. 154(b) by 0 days.

(21) Appl. No.: 13/323,643

(22) Filed: Dec. 12, 2011

(65) Prior Publication Data

US 2013/0150396 A1    Jun. 13, 2013

(51) Int. Cl.
  *A01N 37/18*  (2006.01)
  *A61K 31/16*  (2006.01)
  *A61K 31/165* (2006.01)

(52) U.S. Cl.
  USPC ........... 514/289; 514/613; 514/620; 514/625; 514/629

(58) Field of Classification Search
  USPC ........... 514/772.4, 772.5, 937, 962, 613, 620, 514/625, 629
  See application file for complete search history.

(56) References Cited

U.S. PATENT DOCUMENTS

| | | | | |
|---|---|---|---|---|
| 5,484,606 A | * | 1/1996 | Dhabhar | 424/455 |
| 5,773,031 A | * | 6/1998 | Shah et al. | 424/497 |
| 2003/0171264 A1 | | 9/2003 | Naicker et al. | |
| 2005/0037091 A1 | | 2/2005 | Lindley | |
| 2005/0191343 A1 | | 9/2005 | Liang | |
| 2006/0240051 A1 | * | 10/2006 | Singleton | 424/400 |
| 2010/0010101 A1 | * | 1/2010 | Cherukuri | 514/770 |
| 2010/0068282 A1 | | 3/2010 | Elphick | |
| 2010/0288665 A1 | * | 11/2010 | Lomaga | 206/438 |
| 2011/0117019 A1 | | 5/2011 | Hawkins | |

OTHER PUBLICATIONS

Kerwin, B. A., Polysorbates 20 and 80 Used in the Formulation of Protein Biotherapeutics: Structure and Degradation Pathways. Journal of Pharmaceutical Sciences 97, 2924-2935, published Aug. 2008.*

PCT/US2012/069298—International Search Report and Written Opinion dated Mar. 27, 2013.

* cited by examiner

*Primary Examiner* — Brandon J Fetterolf
*Assistant Examiner* — George W Kosturko
(74) *Attorney, Agent, or Firm* — Dale F. Regelman; Quarles & Brady LLP

(57) ABSTRACT

A composition for increasing the bioavailability of Acetaminophen in humans and animals, comprising Acetaminophen, a first water soluble surfactant having a cloud point greater than about 37° C., a second water soluble surfactant having a cloud point greater than about 37° C., wherein a mixture of the first surfactant and the second surfactant comprises a cloud point less than about 37° C.

4 Claims, No Drawings

SOLUBILIZATION AND BIOAVAILABILITY OF ACETAMINOPHEN

TECHNICAL FIELD

The present invention relates to the solubilization and bioavailability of Acetaminophen and, further, including, optionally, additional drug products, and more particularly to a composition for solubilizing Acetaminophen in a pH independent, non-ionic, anhydrous composition that enables the increased bioavailability of Acetaminophen and optional additional drug products, and a method for making same.

BACKGROUND ART

Drug delivery is the method or process of administering an active pharmaceutical ingredient ("API") to achieve a therapeutic effect in humans or animals. The most common routes of administration include the peroral (through the mouth), topical, transmucosal (nasal, buccal/sublingual, vaginal, ocular and rectal), intra-muscular injection, arterio/venous injection, and inhalation.

Historically, pharmaceutical compositions have primarily consisted of simple, fast-acting chemical compounds. More recently, however, formulations that control the rate and period of drug delivery have become increasingly common and complex.

Current methods of drug delivery exhibit specific problems. For example, many API's potencies and therapeutic effects are limited or otherwise reduced because of the partial degradation that occurs before these APIs reach a desired target. This partial degradation can lead to a need for increased dosages in an attempt to reach a therapeutically acceptable level of available drug. This, in turn, can lead to an increase in side effects and adverse events.

Accordingly, there has been a long felt un-meet need to create an economical, stable drug delivery system that overcomes the need for heat and mechanical energy in its preparation, while at the same time increasing the bioavailability of APIs without altering the API itself, and while obtaining the goal of delivering the API at the lowest therapeutically acceptable level.

Acetaminophen is an analgesic (pain reliever) and antipyretic (fever reducer)medication used to relieve mild to moderate pain such as headaches, muscle aches, menstrual periods, colds and sore throats, toothaches, backaches, osteoarthritis, and reactions to vaccinations, and to reduce fever. Acetaminophen is sold under several branded and generic labels, the most famous likely being TYLENOL sold by the Johnson and Johnson Company of New Brunswick, N.J., a division of McNeil-PPC, Inc.

Acetaminophen is a white, crystalline powder and is a synthetic, nonopiate, centrally acting analgesic derived from p-aminophenol. Its full chemical name is N-acetyl-p-aminophenol. While commonly referred to as Acetaminophen, it has several chemical synonyms, including 4'-hydroxyacetanilide; Paracetamol; Paracetamolo; Paracetamole; P-acetamido-Phenol; 4'-hydroxyacetanilide; n-(p-Hydroxyphenyl)-Acetamide; N-(4-hydroxyphenyl)-Acetamide; P-acetamidophenol; 4-Acetamidophenol; Acetaminofen; P-Acetaminophenol; N-acetyl-p-aminophenol; P-Acetylamino Phenol; P-hydroxyacetanilide; Paracetamol; 4-hydroxy Acetanilide; 4-hydroxyanilid KyselinyOctove; N-(4-hydroxyphenyl)Acetamid, and is sometimes referred to in the industry as APAP.

SUMMARY OF THE INVENTION

A composition for increasing the bioavailability of Acetaminophen in humans and animals is presented. The composition comprises Acetaminophen, a first water soluble surfactant having a cloud point greater than about 37° C., and a second water soluble surfactant having a cloud point greater than about 37° C., wherein a mixture of the first surfactant and the second surfactant comprises a cloud point less than about 37° C.

A composition for increasing the bioavailability of Acetaminophen in humans and animals formed by a process is presented. The process comprises heating polyethylene glycol to about 60° C., adding tocopheryl polyethylene glycol succinate to said heated polyethylene glycol; adding polyoxyethylene sorbitan monooleate to said heated polyethylene glycol and tocopheryl polyethylene glycol succinate; adding polyvinylpyrrolidone to said heated polyethylene glycol, tocopheryl polyethylene glycol succinate, and polyoxyethylene sorbitan monooleate; adding Acetaminophen to said heated polyethylene glycol, tocopheryl polyethylene glycol succinate, polyoxyethylene sorbitan monooleate, polyvinylpyrrolidone; and cooling to room temperature a solution of Acetaminophen, polyethylene glycol, tocopheryl polyethylene glycol succinate, polyoxyethylene sorbitan monooleate, and polyvinylpyrrolidone.

DETAILED DESCRIPTION OF PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Acetaminophen is utilized in many dosage forms, including in suspension or solution (liquid), drops (concentrated liquid), powder, extended-release (long-acting) tablet, orally disintegrating tablet (tablet that dissolves quickly in the mouth), gelcap, and suppository.

Oral dosage form Acetaminophen manufacturers continually seek out ways to package their products in small, easy to swallow formats. These formats help in patient compliance and also may help increase sales for the over-the-counter market. One of the drawbacks to solubilizing Acetaminophen is that its chemical structure makes it difficult to solubilize to any significant degree. Acetaminophen is a stable molecule having structure V:

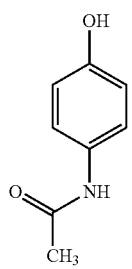

V

Prior art solubilizing efforts include forming a water-soluble salt, such as sodium salt VI. This chemistry is necessarily pH dependent. A shortcoming of ionizing Acetaminophen V is that it alters the Acetaminophen molecule, thus negatively impacting the potency and efficacy of the drug.

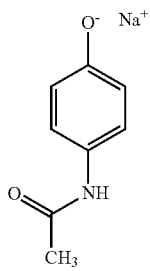

VI

Sodium Acetaminophen VI, comprises a less potent form of the drug V. A less potent drug results in a less effective drug.

A well-understood example of this potency diminution is found in another analgesic, namely salicylic acid for topical use. In its full potential non-ionized state, salicylic acid has excellent keratolytic and penetration properties. However, once it is ionized, it begins to lose it keratolytic properties but does maintain some penetration properties.

In addition to use of Acetaminophen as a single active pharmaceutical ingredient ("API"), Acetaminophen is often mixed with other APIs to treat cough and cold symptoms, aid in sleep, for more severe pain, allergies, and others. Non-limiting examples of APIs added to Acetaminophen include diphenhydramine hydrochloride, phenylephrine hydrochloride, dextromethorphan hydrobromide, guaifenesin and doxylamine succinate.

Accordingly, there has been a long felt need for a composition and method to solubilize significant concentrations of Acetaminophen in a pH independent, non-ionic, anhydrous environment that also enhances bioavailability in a small, easy to swallow format. There is an additional need for such a composition and method that also allows for the combining of other APIs with the Acetaminophen to create products for treating various maladies. The present invention presents such a composition.

In certain embodiments, Applicant's composition for increasing the bioavailability of Acetaminophen comprises a non-ionic surfactant comprising an HLB value in the range of about 12 to about 20. A non-limiting group of non-ionic surfactants meeting this criteria includes polyethylene glycol esters, propylene glycol esters, ethoxylated sorbitan esters, poloxamers, ethoxylated castor oils, ethoxylated lanolin, ethoxylated fatty alcohols, ethoxylated fatty acids, medium chain fatty acids, polyoxylglycerides, glyceride-peg esters, and block polymer non-ionic surfactants.

Cloud point is the temperature above which an aqueous solution of a water-soluble surfactant becomes turbid. Generally, nonionic surfactants show optimal effectiveness when used near or below their cloud point.

Cloud points are typically measured using 1% aqueous surfactant solutions. Cloud points range from 0° to 100° C. (32 to 212° F.), limited by the freezing and boiling points of water. Cloud points are characteristic of nonionic surfactants. Anionic surfactants (with negatively charged groups) are more water-soluble than nonionic surfactants and will typically have much higher cloud points (above 100° C.). The presence of other components in a formulation can depress or increase the solution's cloud point.

Cloud point is also a measure of the hydrophilic/lipophilic balance of a surface-active agent. When a surfactant can have its cloud point run in an aqueous solution, it is therefore a water soluble surface active agent; whereas, when a surfactant must have its cloud point run in an aqueous/solvent mixture, it is either water dispersible or oil soluble in character. Nonionic surface-active agents are less soluble at elevated temperatures in aqueous solutions and, therefore, exhibit a cloud point which varies with the hydrophilic/lipophilic balance of the nonionic surface-active agent.

Applicant's composition for increasing the bioavailability of Acetaminophen includes a first surfactant and a second surfactant. In certain embodiments, the first surfactant comprises a cloud point greater than about 37° C. In certain embodiments, the second surfactant comprises a cloud point greater than about 37° C. In certain embodiments, both the first surfactant and the second surfactant individually comprise cloud points greater than about 37° C. In certain embodiments, the first surfactant comprises a HLB between about 14 and about 16. In certain embodiments, the second surfactant comprises a HLB between about 14 and about 16. In certain embodiments, both the first surfactant and the second surfactant individually comprises a HLB between about 14 and about 16.

In certain embodiments, Applicant's first surfactant comprises an ethoxylated carbohydrate moiety. In certain embodiments, Applicant's first surfactant comprises structure I, wherein a, b, c, d, e, and f, are independently between 0 and about 20. R1, R2, R3, R4, R5, and R6, are selected from the group consisting of H and —CO—R7, wherein R7-COOH comprises a fatty acid. In certain embodiments, R7-COOH is selected from the group consisting of Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, and Docosahexaenoic acid.

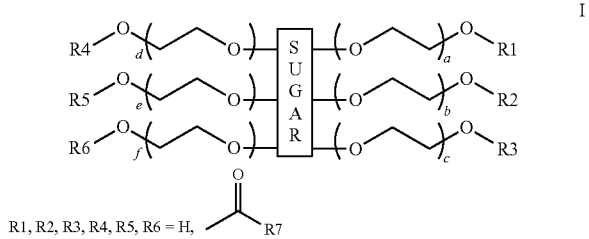

I

Sorbitol, also known as glucitol, SORBOGEM and SORBO, is a sugar alcohol that the human body metabolizes slowly. It can be obtained by reduction of glucose, changing the aldehyde group to a hydroxyl group. Sorbitol is found in apples, pears, peaches, and prunes.

Sorbitan is a mixture of chemical compounds derived from the dehydration of sorbitol. The mixture can vary, but usually consists of 1,4-anhydrosorbitol, 1,5-anhydrosorbitol and 1,4,3,6-dianhydrosorbitol. Sorbitan is primarily used in the production of surfactants such as polysorbates.

Sorbitan esters (also known as Spans) are lipophilic non ionic surfactants that are used as emulsifying agents in the preparation of emulsions, creams, and ointments for pharmaceutical and cosmetic use. When used alone they produce stable water-in-oil emulsions but they are frequently used with a polysorbate in varying proportions to produce water-in-oil or oil-in-water emulsions or creams with a variety of different textures and consistencies. Sorbitan esters are also used as emulsifiers and stabilizers in food In certain embodiments, Applicant's first surfactant comprises a carbohydrate moiety. In certain embodiments, Applicant's first surfactant comprises a polysorbate having structure II, wherein w is between about 1 to about 20 and wherein x, y, and z, are each between 0 to about 20, and wherein R7 is defined hereinabove.

Compound III comprises an average molecular weight of about 1310, a micellar average molecular weight of about 79,900, an aggregation number of about 60, a cloud point of about 65° C., and a HLB of about 15.

In certain embodiments, Applicant's second surfactant comprises a vitamin moiety. In certain embodiments, Applicant's second surfactant comprises an ethoxylated vitamin composition. In certain embodiments, Applicant's second surfactant comprises an esterified Vitamin E composition. In certain embodiments, Applicant's second surfactant comprises tocopheryl polyethylene glycol succinate IV, wherein n is between about 10 to about 100.

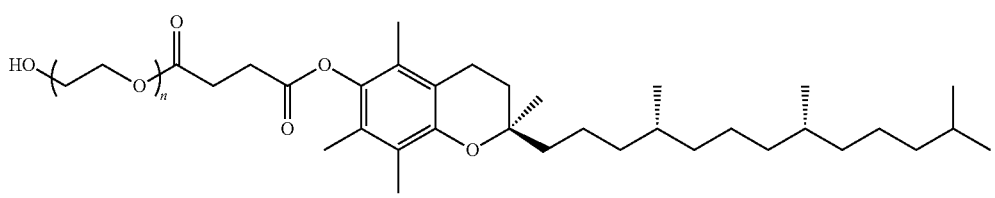

IV

Tocopheryl polyethylene glycol succinate comprises a cloud point of between 62° C. and about 75° C. at concentrations of from about 0.05 weight percent to about 15 weight percent, respectively. Tocopheryl polyethylene glycol succinate comprises a HLB of about 13.

In certain embodiments, Applicant's composition for increasing the bioavailability of Acetaminophen comprises a first surfactant comprising a cloud point greater than about 37° C., and a second surfactant comprising a cloud point greater than about 37° C., wherein a mixture of the first surfactant and the second surfactant comprises a cloud point less than 37° C.

Surfactant molecules self-associate in dilute aqueous solutions to generate aggregates of various types, shapes, and sizes such as small globular micelles, large cylindrical micelles, and spherical vesicles. The characteristics of the aggregates formed are determined by the molecular structure of the surfactant as well as by the solution conditions such as concentration, temperature, ionic strength, and the like.

In certain embodiments, the second surfactant enhances the ability of the first surfactant to form micelles in water. In certain embodiments, the first surfactant comprises a first critical micelle concentration, wherein the combination of the first surfactant and the second surfactant comprises a second critical micelle concentration, wherein the second critical

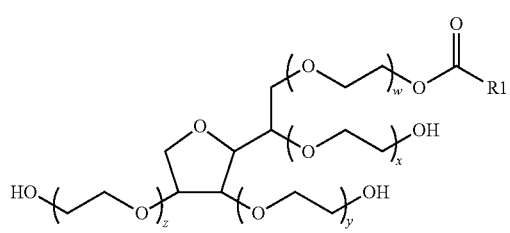

II

In certain embodiments, Applicant's first surfactant comprises polyoxyethylene sorbitan monooleate III.

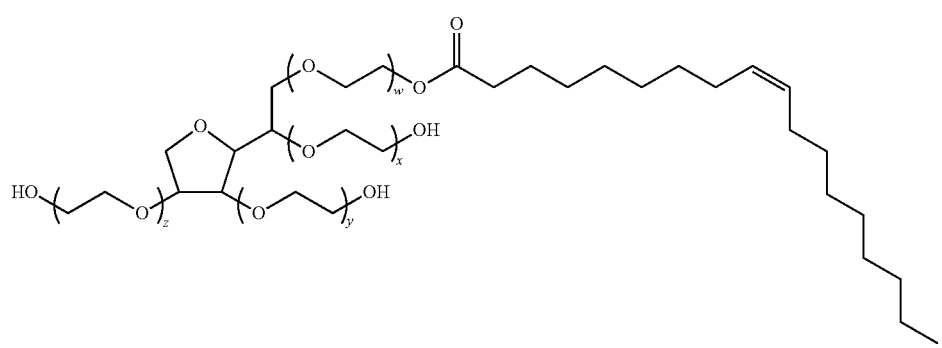

III $w + x + y + z = 20$ micelle concentration is less than the first critical micelle concentration. In certain embodiments, the first surfactant comprises a first critical micelle temperature, wherein the combination of the first surfactant and the second surfactant comprises a second critical micelle temperature, wherein the second critical micelle temperature is less than the first critical micelle temperature.

In certain embodiments, the first surfactant forms a first micelle comprising a first micellar average molecular weight. The combination of the first surfactant and the second surfactant forms a mixed micelle comprising a mixed micellar average molecular weight, wherein the first micellar average molecular weight differs from the mixed micellar average molecule weight.

In certain embodiments, Applicant's composition for increasing the bioavailability of Acetaminophen further comprises a solubilizer. Applicant has discovered that polyethoxylated castor oil, polyethylene glycols, propylene glycol, fatty acids and esters, ethoxylated fatty acids and esters, alcohols, and their derivatives, either singly or in combination, will facilitate solubilization of Acetaminophen in Applicant's first surfactant and second surfactant mixture.

Applicant's composition for increasing the bioavailability of Acetaminophen is particularly suited for gel caps. The present invention comprises a highly concentrated solution of Acetaminophen in a pH independent, anhydrous environment not heretofore seen in the prior art. Applicant's composition for increasing the bioavailability of Acetaminophen comprises a clear, stable end product.

The present invention also provides for the presentation of Acetaminophen in a volume of solution that is small enough to permit easy swallowing. It further provides for the preparation of highly concentrated solutions of the pharmaceutical agent to obtain the same size soft gel capsule for a higher dosage as is presently commercially available for a lower dose soft gel product.

Moreover, the present invention enables the highly concentrated levels of Acetaminophen that can be used alone or in combination with other pharmaceutical agents, such as antihistamines, antitussives, decongestants, expectorants, and pain medications to form a clear solution for encapsulation into a soft gel.

In certain embodiments, Applicant's composition for increasing the bioavailability of Acetaminophen comprises between about 30 weight percent to about 48 weight percent Acetaminophen, between about 30 weight percent to about 50 weight percent polyethylene glycol, between about 6 weight percent to about 12 weight percent tocopheryl polyethylene glycol succinate, greater than about 5 weight percent polyvinylpyrrolidone, and between about 1 weight percent and about 3 weight percent polysorbate.

In certain embodiments, polyethylene glycol is heated to greater than about 60° C. Tocopheryl polyethylene glycol succinate, polyoxyethylene sorbitan monooleate, and polyvinylpyrrolidone are then added. Acetaminophen is admixed into the solution.

Applicant's composition for increasing the bioavailability of Acetaminophen can be utilized in multiple routes of administration. For example and without limitation, Applicant's composition for increasing the bioavailability of Acetaminophen, in optional combination with one or more APIs, can be administered in a soft gel capsule or in a liquid formulation.

The following examples are presented to further illustrate to persons skilled in the art how to make and use the invention. The following examples are not intended as limitations, however, upon the scope of the invention, which is defined by the claims appended hereto.

EXAMPLE I

A first embodiment of Applicant's composition for increasing the bioavailability of Acetaminophen was formed as described hereinabove wherein 300 milligrams of polyethylene glycol 400 (40.3% by weight) was heated to about 60° C. Thereafter, 100 milligrams of tocopheryl polyethylene glycol succinate (13.4% by weight), 20 milligrams of polyoxyethylene sorbitan monooleate (2.7% by weight), and 325 milligrams of Acetaminophen (43.6% by weight) were added. The resulting composition formed a solution, but a precipitate fell out of solution at about 60 minutes.

EXAMPLE II

A second embodiment of Applicant's composition for increasing the bioavailability of Acetaminophen was formed as described hereinabove wherein 260 milligrams of polyethylene glycol 400 (35.4 weight percent) was heated to about 60° C. Thereafter, 70 milligrams of tocopheryl polyethylene glycol succinate (9.5 weight percent), 10 milligrams of polyoxyethylene sorbitan monooleate (1.4 weight percent), 70 milligrams of polyvinylpyrrolidone (9.5 weight percent), and 325 milligrams of Acetaminophen (44.2 weight percent) were added. The resulting composition formed a solution. No precipitate formed upon standing at room temperature.

EXAMPLE III

A third embodiment of Applicant's composition for increasing the bioavailability of Acetaminophen was formed as described hereinabove wherein 260 milligrams of Polyethylene glycol 400 (35.4 weight percent) was heated to about 60° C. Thereafter, 60 milligrams of tocopheryl polyethylene glycol succinate (8.2 weight percent), 20 milligrams of polyoxyethylene sorbitan monooleate (2.7 weight percent), 70 milligrams of polyvinylpyrrolidone (9.5 weight percent), and 325 milligrams of Acetaminophen (44.2 weight percent) were added. The resulting composition formed a solution. No precipitate formed upon standing at room temperature.

EXAMPLE IV

A fourth embodiment of Applicant's composition for increasing the bioavailability of Acetaminophen was formed as described hereinabove wherein 265 milligrams of Polyethylene glycol 400 (36.1 weight percent) was heated to about 60° C. Thereafter, 60 milligrams of tocopheryl polyethylene glycol succinate (8.2 weight percent), 15 milligrams of polyoxyethylene sorbitan monooleate (2.0 weight percent), 70 milligrams of polyvinylpyrrolidone (9.5 weight percent), and 325 milligrams of Acetaminophen (44.2 weight percent) were added. The resulting composition formed a solution. No precipitate formed upon standing at room temperature.

In other embodiments of Applicant's composition for increasing the bioavailability of Acetaminophen, one or more additional active pharmaceutical ingredients ("APIs") are added to the compositions of Examples I, II, III, and IV. For example, in certain embodiments diphenhydramine hydrochloride, phenylephrine hydrochloride, dextromethorphan hydrobromide, guaifenesin and doxylamine succinate are added to Applicant's composition for increasing the bioavailability of Acetaminophen of Examples I, II, III, and IV.

EXAMPLE V

In certain embodiments, Phenylephrine hydrochloride and Dextromethorphan hydrobromide are added to the Acetaminophen composition by admixing the two pharmaceuticals together in combination with Applicant's composition for increasing the bioavailability of Acetaminophen of Examples I, II, III, and IV. In certain embodiments, 5 milligrams of Phenylephrine hydrochoride (0.6 weight percent) and 10 milligrams of Dextromethorphan hydrobromide (1.3 weight percent) are added to about milligrams of polyethylene glycol. This mixture is then added to any one of Applicant's composition for increasing the bioavailability of Acetaminophen of Examples I, II, III, and IV.

EXAMPLE VI

In certain embodiments, Phenylephrine hydrochoride, Dextromethorphan hydrobromide, and Doxylamine succinate are added to Applicant's composition for increasing the bioavailability of Acetaminophen of Examples I, II, III, IV, and V, by admixing the two pharmaceuticals with polyethylene glycol and then adding the combination to Applicant's composition for increasing the bioavailability of Acetaminophen of Examples I, II, III, IV, and V. In certain embodiments, Doxylamine succinate is admixed with about 30 milligrams of polyethylene glycol, and that mixture is added to Applicant's composition for increasing the bioavailability of Acetaminophen of Example V.

EXAMPLE VII

In certain embodiments, 5 milligrams of Phenylephrine hydrochloride, 10 milligrams of Dextromethorphan hydrobromide (about 1 weight percent), 10 mg of Dextromethorphan hydrobromide (about 1 weight percent), and 200 mg of Guaifenesin (about 18 weight percent) are added to Applicant's composition for increasing the bioavailability of Acetaminophen of Examples I, II, III, or IV. the three additional APIs are admixed with about 170 milligrams of polyethylene glycol before being added to the Acetaminophen composition. To decrease the overall amount of Applicant's composition for increasing the bioavailability of Acetaminophen of Examples I, II, III, or IV. To decrease the overall amount of polyethylene glycol in the final product, it is possible to use a lesser amount of polyethylene glycol in the original Acetaminophen composition and add it to the Phenylephrine hydrochoride, Dextromethorphan hydrobromide, Guaifenesin While the preferred embodiments of the present invention have been illustrated in detail, it should be apparent that modifications and adaptations to those embodiments may occur to one skilled in the art without departing from the scope of the present invention as set forth in the following claims.

I claim:

1. A composition for increasing the bioavailability of Acetaminophen in humans and animals, consisting of:
   Acetaminophen at 43.6 weight percent;
   polyethylene glycol 400 at 40.3 weight percent;
   a first water soluble surfactant having a cloud point greater than about 37° C., wherein said first surfactant is tocopheryl polyethylene glycol succinate at 13.4 weight percent;
   a second water soluble surfactant having a cloud point greater than about 37° C., wherein said second surfactant is polyoxyethylene sorbitan monooleate at 2.7 weight percent;
   wherein said composition comprises a cloud point less than about 37° C.

2. A composition for increasing the bioavailability of Acetaminophen in humans and animals, formed by the process of:
   heating 265 milligrams polyethylene glycol is heated to about 60° C.;
   adding 60 milligrams of tocopheryl polyethylene glycol succinate to said heated polyethylene glycol;
   adding 15 milligrams of polyoxyethylene sorbitan monooleate to said heated polyethylene glycol and tocopheryl polyethylene glycol succinate;
   adding 70 milligrams of polyvinylpyrrolidone to said heated polyethylene glycol, tocopheryl polyethylene glycol succinate, and polyoxyethylene sorbitan monooleate;
   adding 325 milligrams of Acetaminophen to said heated polyethylene glycol, tocopheryl polyethylene glycol succinate, polyoxyethylene sorbitan monooleate, polyvinylpyrrolidone;
   cooling to room temperature a solution of Acetaminophen (44.2 weight percent), polyethylene glycol (36.1 weight percent), tocopheryl polyethylene glycol succinate (8.2 weight percent), polyoxyethylene sorbitan monooleate (2.0 weight percent), and polyvinylpyrrolidone (9.5 weight percent);
   wherein:
   said tocopheryl polyethylene glycol succinate has a cloud point greater than 37° C.;
   said polyoxyethylene sorbitan monooleate has a cloud point greater than 37° C.; and
   said solution has a cloud point less than 37° C.

3. A composition for increasing the bioavailability of Acetaminophen in humans and animals, consisting of:
   Acetaminophen at 44.2 weight percent;
   polyethylene glycol 400 at 35.4 weight percent;
   a first water soluble surfactant having a cloud point greater than about 37° C., wherein said first surfactant is tocopheryl polyethylene glycol succinate at 9.5 weight percent;
   a second water soluble surfactant having a cloud point greater than about 37° C., wherein said second surfactant is polyoxyethylene sorbitan monooleate at 1.4 weight percent;
   polyvinylpyrrolidone at 9.5 weight percent;
   wherein said composition has a cloud point less than about 37° C.

4. A composition for increasing the bioavailability of Acetaminophen in humans and animals, consisting of:
   Acetaminophen at 44.2 weight percent;
   polyethylene glycol 400 at 35.4 weight percent;
   a first water soluble surfactant having a cloud point greater than about 37° C., wherein said first surfactant is tocopheryl polyethylene glycol succinate at 8.2 weight percent;
   a second water soluble surfactant having a cloud point greater than about 37° C., wherein said second surfactant is polyoxyethylene sorbitan monooleate at 2.7 weight percent;
   polyvinylpyrrolidone at 9.5 weight percent;
   wherein said composition has a cloud point less than about 37° C.

* * * * *